United States Patent [19]

Matthews et al.

[11] Patent Number: 5,252,836
[45] Date of Patent: Oct. 12, 1993

[54] REFLECTIVE GRAIN DEFECT SCANNING

[75] Inventors: Peter C. Matthews, Poole; Barry G. Wilson, Broadstone, both of United Kingdom; Jon F. Soest, Sumner, Wash.

[73] Assignee: U.S. Natural Resources, Inc., Vancouver, Wash.

[21] Appl. No.: 906,537

[22] Filed: Jun. 30, 1992

Related U.S. Application Data

[63] Continuation-in-part of Ser. No. 666,133, Mar. 7, 1991, abandoned.

[51] Int. Cl.$^5$ ............................................. G01N 21/86
[52] U.S. Cl. ..................................... 250/571; 250/572; 356/445; 356/446
[58] Field of Search ................. 250/571, 572; 356/445, 356/446

[56] References Cited

U.S. PATENT DOCUMENTS

| | | | |
|---|---|---|---|
| 3,850,526 | 11/1974 | Corey, III | 250/571 |
| 3,922,093 | 11/1975 | Dandliker et al. | 250/571 |
| 4,276,910 | 7/1981 | Eichenberger | 250/571 |
| 4,606,645 | 8/1986 | Matthews et al. | 356/446 |
| 4,710,642 | 12/1987 | McNeil | 250/571 |
| 4,754,148 | 6/1988 | Barkowski et al. | 250/571 |
| 4,945,253 | 7/1990 | Frohardt | 250/571 |

Primary Examiner—Paul M. Dzierzynski
Assistant Examiner—Kiet T. Nguyen
Attorney, Agent, or Firm—Robert L. Harrington

[57] ABSTRACT

Grain structure defect scanning is accomplished by a pair of light detectors directed toward an inspection point illuminated by a collimated light beam incident upon the inspection surface at a given angle of incidence. One detector, the specular detector, is positioned generally along the specular angle of reflection as defined by the angle of incidence and the other detector, the diffuse detector, lies substantially along the angle of incidence. When specular reflection dominates, as when the inspection point corresponds to clearwood, the specular detector indicates a higher reflective light intensity than the diffuse detector. When diffuse reflection dominates, however, as when the inspection point corresponds to a grain defect, both detectors indicate similar reflective light intensity. Grain defect discrimination is accomplished by calculating a ratio of specular detector output to diffuse detector output. Further analysis of the relative magnitudes of the detector outputs provides a basis for identifying grading marks, such as ink and wax marks, at the inspection point.

24 Claims, 7 Drawing Sheets

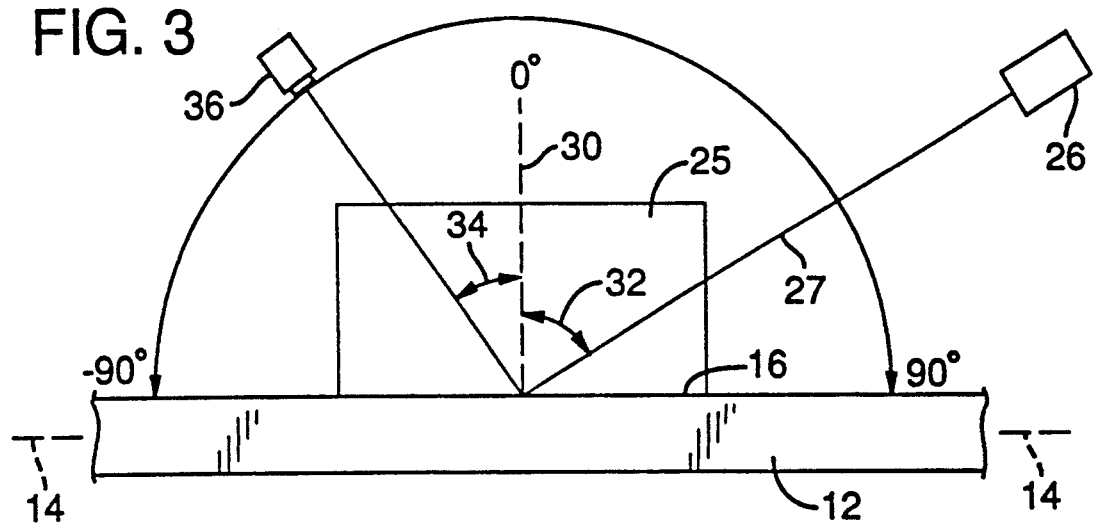
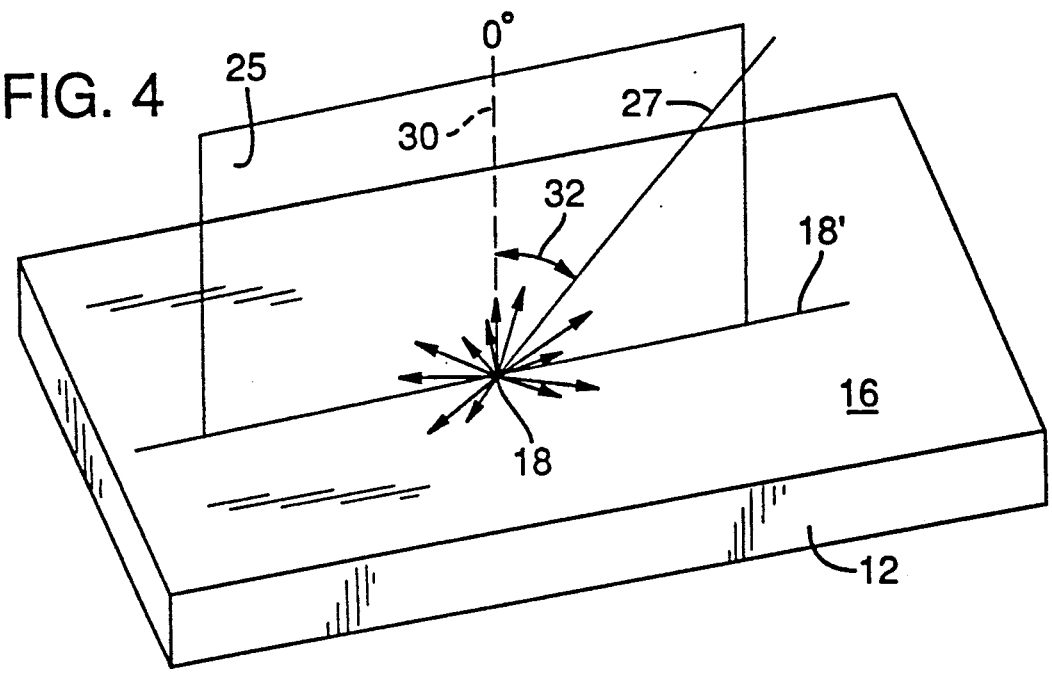
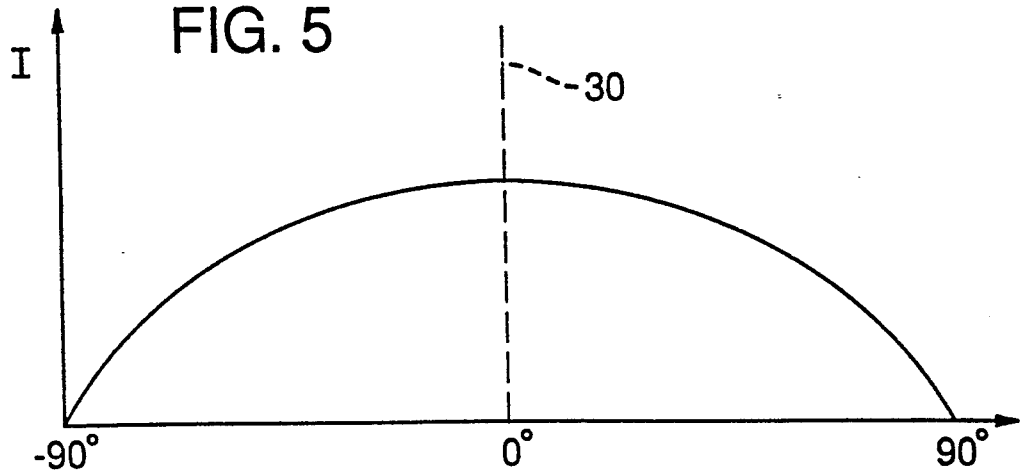

REFLECTIVE GRAIN DEFECT SCANNING

RELATED APPLICATIONS

The present application is a continuation-in-part of co-pending U.S. patent application Ser. No. 07/666,133 filed Mar. 7, 1991, now abandoned, by applicants herein and assigned in common to the assignee hereof.

FIELD OF THE INVENTION

The present invention relates to wood product processing and particularly to a method and apparatus for detection of grain defects by reflective scanning.

BACKGROUND OF THE INVENTION

Automatic detection of grain defects improves wood processing operations. Overall production efficiency and product quality can be increased by automatic grain defect detection and corresponding product grading, processing, or remedial action. Unfortunately, existing defect scanning techniques have been complex and, therefore, not always available where the benefit of automatic grain defect detection does not outweigh the expense of such scanning techniques. For example, grain defect scanning of plywood panels or solid lumber would improve production, but cannot be accomplished by through-grain scanning techniques and must be accomplished by relatively more complicated and expensive reflective scanning methods. Grain defect scanning of panels and solid wood material has not been regarded as feasible because of the complexity and expense of heretofore available reflective scanning technologies.

U.S. Pat. No. 4,606,645 issued Aug. 19, 1986 to applicants herein, Peter C. Matthews and Jon F. Soest, shows characteristics of light energy reflection from a wood grain article for the purpose of detecting wood grain orientation. In that disclosure, a light beam is directed along a path normal to the surface of the wood grain article. No provision is shown for detecting light energy along a path corresponding to a specular line of reflection. The disclosure of U.S. Pat. No. 4,606,945 is considered pertinent for its teaching of light energy reflection for a wood grain structure.

U.S. Pat. No. 4,754,148 issued Jun. 28, 1988 to Barkowski et al and entitled ADJUSTABLY POSITIONED APPARATUS MAINTAINING A FIXED PERPENDICULAR DISTANCE FOR EVALUATING A CURVED SURFACE shows a method of evaluating a surface finish. More particularly, the Barkowski method judges the appearance of a metallic surface, and is not believed suitable for the evaluation of wood grain surface structure features. In the method of Barkowski, the smoothness of a surface, referred to as "haze", is detected by comparing the intensity of light reflected exactly along the specular direction with the intensity of light reflected along directions very close to, viz., within several degrees of, the specular direction. By computing a ratio of the reflected light energies, the surface finish of the article under inspection is evaluated.

The essence of the Barkowski method is the evaluation of a finish of a curved surface from a fixed height and at a fixed angle regardless of the surface curvature. Detecting at exactly the specular reflection angle is an essential element of the Barkowski method, and for this reason the Barkowski method requires precise mechanical structures and optical design criteria to position the detector on exactly the specular line of reflection.

U.S. Pat. No. 3,850,526 issued Nov. 26, 1974 to Cory, III and entitled OPTICAL METHOD AND SYSTEM FOR MEASURING SURFACE FINISH shows a method of measuring the surface roughness of an article. Under the Cory method, a surface finish value is obtained by a selectively positioned detector reading reflection values of a diffraction pattern to obtain integrated values which are then compared with a calibration curve to obtain the surface finish value. In another embodiment of the Cory method, the surface roughness is measured by the difference in the output signal levels from a detector or detectors set to detect the primary and secondary diffraction pattern reflection lobes. The ratio of the intensity of the primary lobe and its first adjacent secondary lobe is considered under the Cory method to be a direct measure of the surface roughness.

U.S. Pat. No. 3,922,093 issued Nov. 25, 1975 to Dandliker et al and entitled DEVICE FOR MEASURING THE ROUGHNESS OF A SURFACE shows a device for illuminating a surface being studied and a photo sensitive detector for determining the maximum intensity of light reflected on the surface. The apparatus further determines two points at which the intensity of the reflected light has fallen relative to the maximum detected intensity. The distance between these two points is then taken as a representation of the roughness of the surface being studied.

U.S. Pat. No. 4,276,910 issued Jul. 7, 1981 to Echenberger and entitled PHOTO ELECTRIC BOBBIN FEELER shows the use of one light source and two light sensors, or two light sources and one light sensor. A polaroid filter is interposed in front of the light source for polarizing the light which is specularly as well as diffusely reflected from the bobbin, and thereby provides a safer detection of the "bobbin empty" condition.

U.S. Pat. No. 4,710,642 issued Dec. 1, 1987 to McNeil and entitled OPTICAL SCATTEROMETER HAVING IMPROVED SENSITIVITY AND BAND WIDTH illustrates a multiple detector array that enables the measurement of sample microstructure over an increased range of spatial frequency. Under the optical scatterometer of McNeil a laser beam is directed toward a sample along a first line. A first array of optical detectors is positioned in the plane of the laser beam, but along its specular line of reflection. A second array of optical detectors is positioned along the line of the laser beam to detect forward scattered light within the plane of the laser beam.

U.S. Pat. No. 4,945,253 issued Jul. 31, 1990 to Frohardt and entitled MEANS OF ENHANCING THE SENSITIVITY OF A GLOSS SENSOR shows an arrangement for optically measuring the gloss or reflectance of a surface. The gloss sensor includes a light source emitting a light beam toward a surface to be measured. The gloss sensor also includes a light detecting device arranged to detect the intensity of the diffusely reflected component of the reflected light beam relative to the specularly reflected component.

A simple and relatively low cost reflective grain defect scanning method and apparatus would make available the benefits of automated grain defect detection in the production of, for example, plywood panels and hardwood stock.

SUMMARY OF THE INVENTION

Grain structure defects are not ordinarily a quality of surface finish, but rather a quality of the fiber structure under inspection. It is desirable, therefore, that the evaluation of grain structure defects be substantially independent of surface appearance. Such a grain defect method provides great utility in the context of wood grain structural defect detection. Much of the prior art in the field of wood grain defect detection methods have failed because such prior methods have used surface appearance as a basis for evaluating defects in grain structure.

In accordance with the present invention, the surface structures of a wood grain article are characterized by computing a ratio of specular reflection to diffuse reflection as measured from separate view angles of a point of incidence of a scanning energy beam. A grain defect is indicated by similar energy reflection magnitudes while clearwood is indicated by a substantially greater specular reflection relative to the diffuse reflection.

Grain defect scanning in accordance with a preferred embodiment of the present invention is accomplished by scanning of an inspection point illuminated by a collimated light beam directed toward an inspection surface at a given angle of incidence. A pair of light detectors provide simultaneous views of the point of incidence as represented by reflected light intensity. One detector, the specular detector, is positioned generally along the specular angle of reflection as defined by the angle of incidence with respect to the inspection surface. The other detector, the diffuse detector, lies substantially along the angle of incidence. Specular reflection from the inspection point dominates when the inspection point corresponds to clearwood. In such case, the specular detector indicates a higher reflective light intensity than the diffuse detector. Diffuse reflection dominates when the inspection point corresponds to a grain defect. Both detectors indicate similar reflective light intensity for diffuse light reflection. Grain defect discrimination is accomplished by calculating a ratio of specular detector output to diffuse detector output whereby a ratio substantially greater than unity indicates clearwood and a ratio close to unity indicates a grain defect at the inspection point.

BRIEF DESCRIPTION OF THE DRAWINGS

FIG. 3 is a reference system used to illustrate two light reflection models believed to account for light reflection from a wood grain surface.

FIG. 4 illustrates in perspective a diffuse light reflection model.

FIG. 5 plots reflected light intensity according to the diffuse light reflection model.

DETAILED DESCRIPTION OF THE INVENTION

Figure 1:
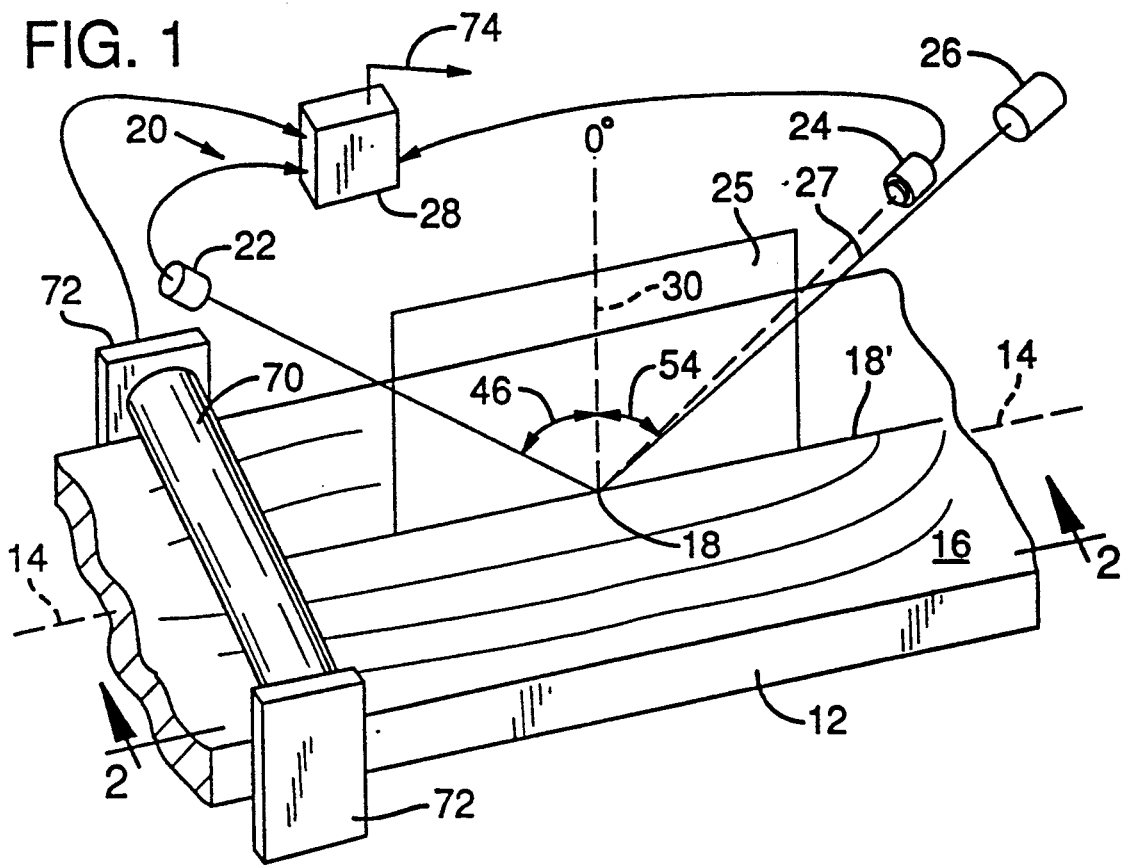
FIG. 1 is a perspective view of a reflective grain defect apparatus according to a first embodiment of the present invention and a wood grain article subject to grain defect inspection.
Figure 2:
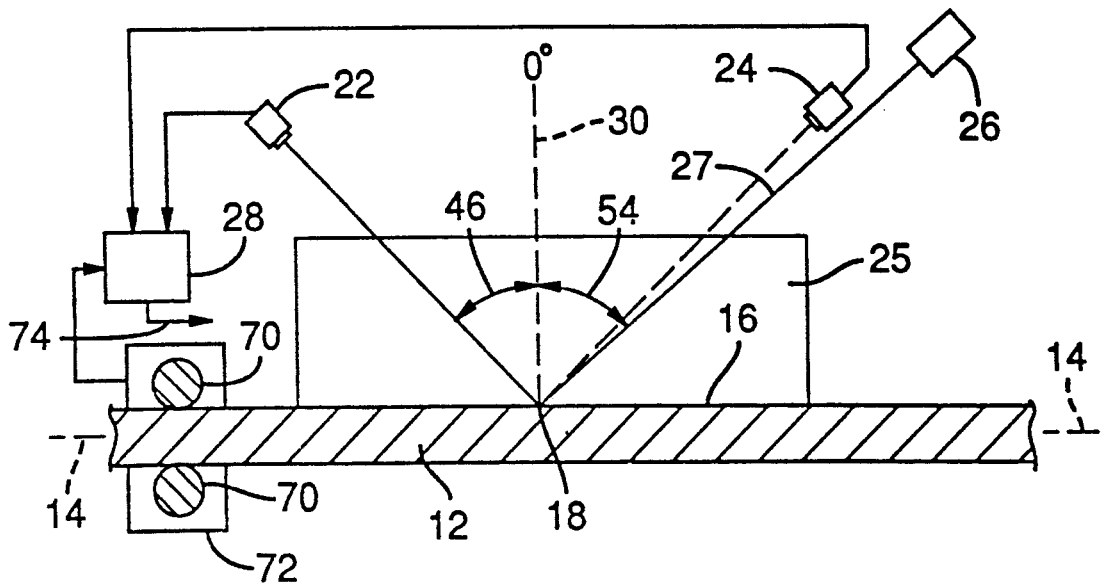
FIG. 2 is a side view of the apparatus and wood grain article taken along lines 2—2 of FIG. 1.

FIGS. 1 and 2 illustrate a first embodiment of the present invention, a grain defect detection apparatus 20 using reflective scanning. In FIGS. 1 and 2, an elongate wood grain article 12, having a longitudinal axis 14 and inspection surface 16, is subject to grain defect scanning at an inspection point 18 of surface 16. As used herein, the term "inspection point" shall refer to a point of incidence of scanning light directed upon an inspection surface, not necessarily a static point on the inspection surface. Article 12 has wood fiber lying substantially along its longitudinal axis 14, but may have grain defects or gross deviations from the normal direction of the wood fiber, e.g., knotwood. Grain defect detection device 20 identifies grain defects at the inspection point 18 of article 12. As discussed more fully below, translation of article 12 relative to apparatus 20 and along longitudinal axis 14, i.e. as in longitudinal material feeding applications, provides grain defect scanning along a line 18' corresponding to a plurality of inspection points 18 as defined by such longitudinal movement.

The embodiment of FIGS. 1 and 2 is essentially a single point or pixel based device adapted for relatively narrow scanning width applications, but illustrates the basic operational principles of the present invention. A second embodiment of the present invention, described below, uses an across grain linescanning technique and arrays of light detectors to implement a more practical, i.e., broader width, grain defect scanning application in accordance with the present invention.

Grain defect detection apparatus 20 includes a pair of light detection devices, detectors 22 and 24, each bearing upon inspection point 18 and lying along the line of material feed, i.e., in the plane of incidence 25 orthogonal to the surface 16 o and containing the line 18'. Detectors 22 and 24 lie 15 symmetrically within plane of incidence 25. The lines of sight to inspection point 18 for each detection device are substantially symmetric about a vertical reference axis 30 which is within plane of incidence 25, normal to surface 16, and coincident with the point 18. A light source 26 directs a collimated light beam 27, e.g. a low power laser beam, toward point 18 and substantially, as close as possible, along the line of sight between detector 24 and inspection point 18. Each detector 22 and 24 produces an output signal representative of a level of reflected light energy detected. A discrimination circuit 28 receives the output from detectors 22 and 24 to identify grain defects at a given inspection point 18. Discrimination circuit 28 may be a general purpose computer or dedicated circuitry adapted in conventional manner to practice the present invention as described herein.

The present invention may be better understood with reference to two light reflection models believed to represent components of light reflected from the structures of a wood grain surface. FIG. 3 provides a reference system, similar in arrangement to that of apparatus 20, useful in illustrating the light reflection models. Beam 27 is represented by its angle of incidence 32 relative to axis 30, and, unless otherwise stated, remains fixed. Reflective light intensity is represented as would be detected by a movable light detector 36 maintained within plane of incidence 25 at a given distance from inspection point 18 and expressed as a function of angular position 34 relative to axis 30. Plotting the output of detector 36, for a fixed angle of incidence 32, against a range of angular positions 34 illustrates the character of each light reflection model.

The first light reflection model, illustrated in FIG. 4, represents diffuse reflection where light reflects in all directions from the point of incidence. FIG. 5 plots reflective light intensity according to the diffuse reflection model for detector 36 having angular positions $-90$ degrees through 90 degrees. The plot function, $I = I_o \cos O$, is an evenly contoured response, symmetric about reference axis 30, and having maxima normal to surface 16, and coincident with axis 30. It is noted that purely diffuse reflection is independent of the angle of incidence 32 for beam 27. Returning briefly to FIGS. 1 and 2, according to the diffuse reflection model detectors 22 and 24, being symmetric about axis 30, will register substantially equal light intensity with respect to diffuse reflection.

Figure 6:
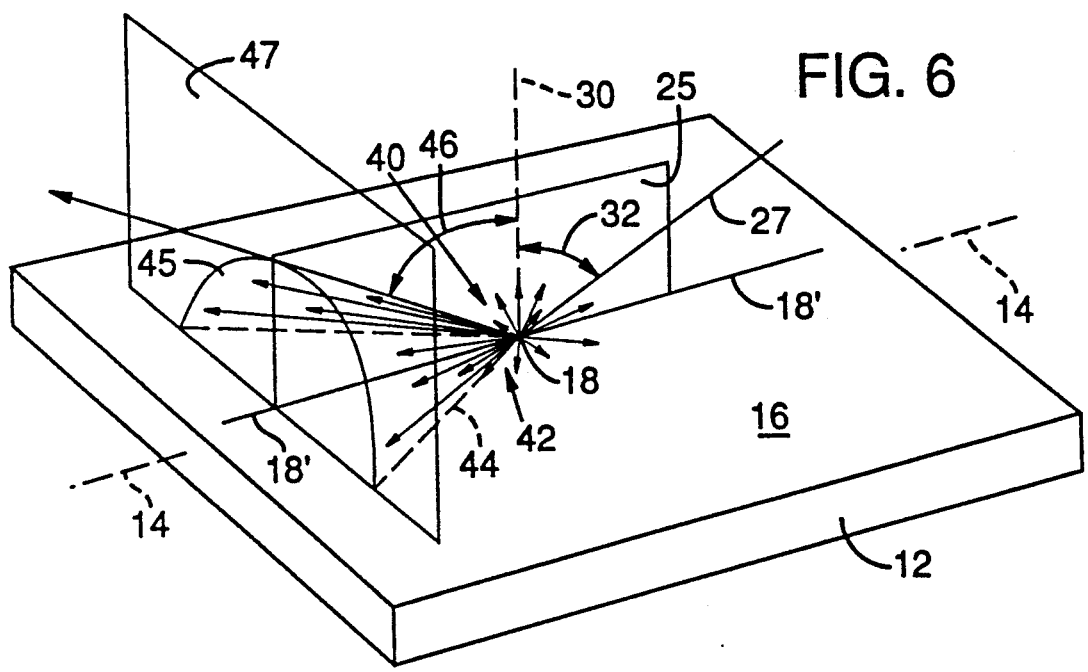
FIG. 6 illustrates in perspective a specular diffuse light reflection model.

The second light reflection model, illustrated in FIG. 6, is termed "specular diffuse", meaning that some of the reflecting light acts as though it undergoes specular or mirror-like reflection while the other components act as though it reflects from a diffuse surface. In FIG. 6, diffuse reflection component 40 emanates from inspection point 18 according to the above described diffuse reflection model. Specular reflection component 42, however, emanates from inspection point 18 along the surface of a cone 44 having a central axis collinear with line 18' and a half angle $(90° - i)$ relative to surface 16 where i equals the angle of incidence 32. Accordingly, the specular component 42 defines a semi-circular arc 45 within a plane 47 orthogonal to surface 16 and to plane of incidence 25. The cone-like shape of the specular component 42 is believed to result from surface 16 having substantially regular surface contour along a first dimension parallel to longitudinal axis 14, i.e., along the length of fiber cells, and an irregular surface contour in a second orthogonal transverse to axis 14, i.e., transverse to the fiber cells. The specular diffuse component of reflected light is believed to be caused primarily by the cellulose fibers in the cell walls, while the diffuse component is caused primarily by the remaining cell structure, cavities, resin, etc.

Figure 7:
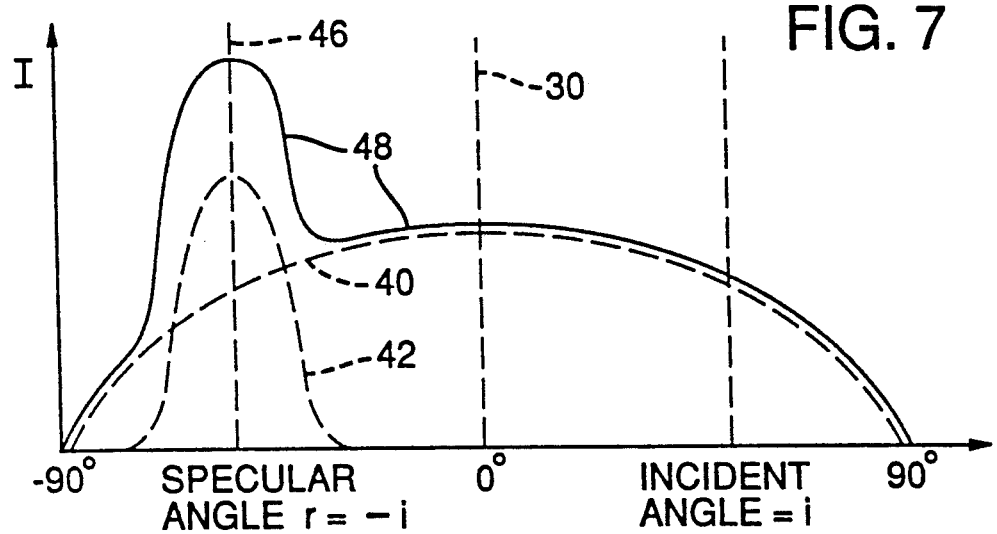
FIG. 7 plots reflected light intensity according to the specular diffuse light reflection model.

FIG. 7 plots light intensity according to the specular diffuse model for a fixed angle of incidence 32 and a range of detector 36 positions from $-90$ degrees through 90 degrees. In FIG. 7, the diffuse component 40 appears, in accordance with the diffuse reflection model, as an evenly contoured response symmetric about axis 30. The specular component 42 appears as a more narrow response centered about a specular reflection angle 46 lying along the surface of cone 44. Note that the specular reflection angle 46 is equal in magnitude to the incident angle 36. The composite reflection response 48, according to the specular diffuse reflection model, generally follows the diffuse component 40, but has a characteristic maximum centered about the specular reflection angle 46.

Experimentation indicates that light reflecting off a wood grain article behaves according to a combination of the diffuse reflection model and the specular diffuse reflection model. More importantly, experimentation has shown that specular diffuse reflection dominates for clearwood reflections and diffuse reflection dominates for grain defect reflections. Grain defect detection according to the present invention discriminates between specular diffuse reflection and diffuse reflection in order to distinguish clearwood and grain defects. Accordingly, grain defect detection is accomplished by discriminating between the substantially symmetric response of FIG. 5 and the asymmetric response of FIG. 7.

Figure 8:
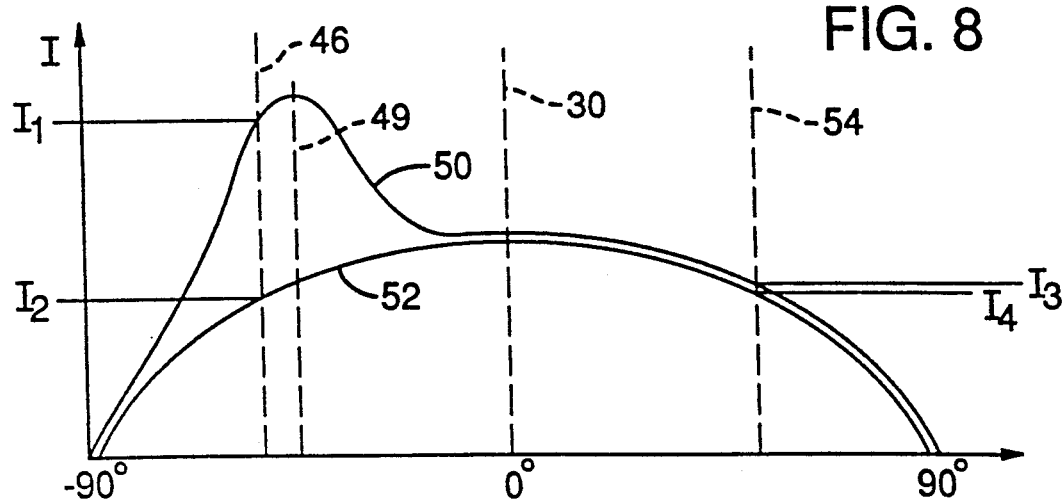
FIG. 8 plots reflected light intensity for clearwood and for grain defects and illustrates the method of distinguishing therebetween in accordance with the present invention.

FIG. 8 plots a typical clearwood function 50 and a typical grain defect function 52. More particularly, function 50 illustrates detector 36 output for an inspection point 18 corresponding to a clearwood portion of surface 16 while function 52 illustrates detector 36 output for an inspection point 18 corresponding to a grain defect portion, e.g., knotwood, of surface 16. The difference between functions 50 and 52 provides a basis for discrimination by apparatus 20 of clearwood versus grain defect wood.

With reference to FIGS. 1, 2 and 8, detectors 22 and 24 of apparatus 20 are placed symmetrically relative to axis 30 and light beam 27 is directed along an incidence angle 54 substantially collinear with the line of sight from detector 22 to inspection point 18. The detector 22 lies generally along the specular reflection angle 46, i.e., close to or along the surface of cone 44 of the specular diffuse reflection model. This arrangement provides two separate angular views of the inspection point 18. Detector 22, the specular detector, is positioned to detect the maximum associated with the specular reflection component 42 of the specular diffuse reflection as well as diffuse reflection. The diffuse detector 24 is positioned to monitor diffuse reflection only.

With detector 22 lying on the angle 46, detector 22 output indicates a light intensity $I_1$ for clearwood and a light intensity $I_2$ for grain defects. Similarly, with detector 24 lying on axis 54, detector 24 indicates a light intensity $I_3$ for clearwood and a light intensity $I_4$ for grain defects. The light intensity values $I_2$, $I_3$ and $I_4$ are substantially equal while the intensity value $I_1$ is relatively greater. Measuring the relative output magnitudes, as suitably calibrated, of detectors 22 and 24 provides a basis for discriminating between clearwood and grain defect wood. In particular, the discrimination function is expressed as the ratio of detector 22 output to detector 24 output where a result substantially greater than unity, e.g., $I_1$ divided by $I_3$, indicates clearwood, and a result substantially near unity, e.g. $I_2$ divided by $I_4$, indicates grain defect wood. Discrimination circuit 28 divides detector 22 output magnitude by detector 24 output magnitude. For a result substantially greater than unity, discrimination circuit 28 identifies the inspection point 18 as corresponding to clearwood, and for a result substantially near unity discrimination circuit 28 identifies the inspection point 18 as corresponding to a grain defect. Typical clearwood yields a ratio of approximately 1.8 to 2 while knotwood yields a ratio near unity. It may be appreciated that discrimination is based on the relative output magnitudes of detectors 22 and 24, not absolute output magnitudes. Accordingly, variations between wood grain patterns of individual wood articles inspected, resulting in different absolute levels of reflected light for individual articles, are substantially masked.

As will be apparent to those skilled in the art, by suitably indexing the position of article 12 relative to apparatus 20 and collecting detector 22 and 24 data for each indexed position it is possible to gather sufficient data to characterize surface 16 as to grain defects along the line 18'. In FIGS. 1 and 2, indexing rollers 70 contact the upper surface 16 and lower surface of article 12 and roller control 72 moves article 12, by way of rollers 70, in indexed fashion while providing article 12 position data to discrimination circuit 28. Discrimination circuit 28 may then associate a physical location on surface 16 with the inspection point 18 for each indexed position of article 12. By such association, the location of detected grain defects may be specified using apparatus 20. Multiple longitudinal scanning passes but across different width portions of surface 16 would provide scanning of the entire surface 16. Discrimination circuit 28 then constructs a data representation 74 of surface 16 as output useful in subsequent wood processing operations to maximize use of article 12. For example, article 12 may be cut into smaller dimension products using knowledge of grain defect positions so as to maximize stress capabilities of the resulting product as by avoiding grain defects near product edges.

While the embodiment of FIGS. 1 and 2 provides an accurate method of grain defect detection, this embodiment may not be practical in most automated wood processing operations.

Figure 9:
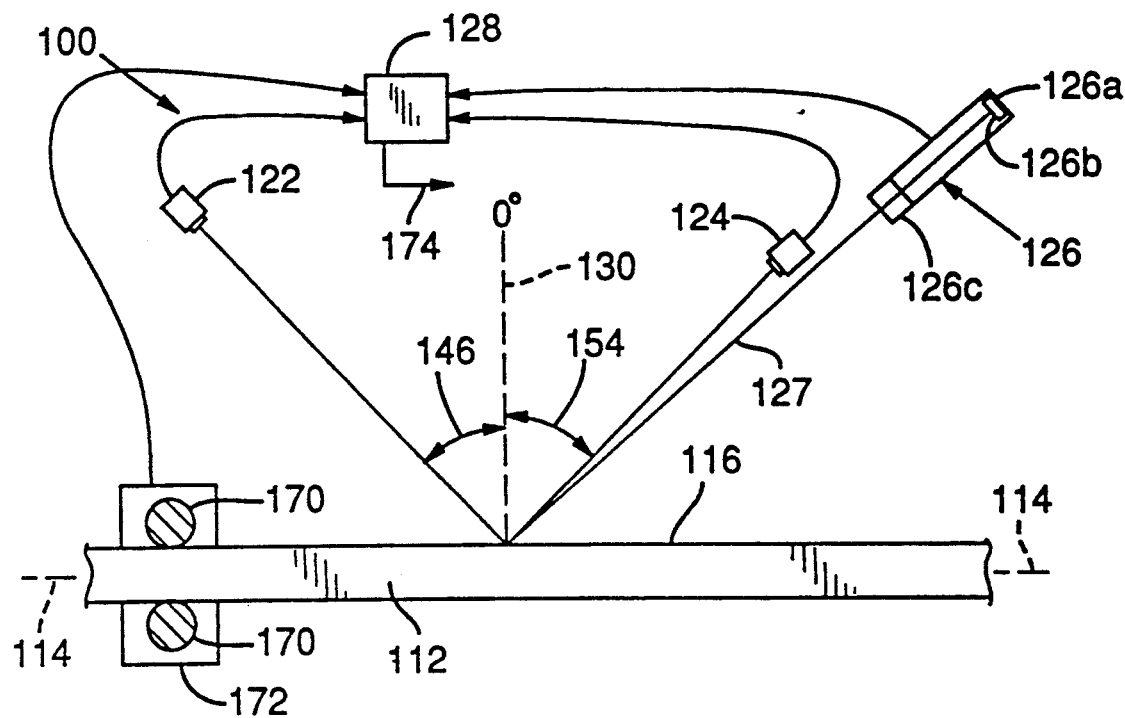
FIGS. 9 and 10 illustrate side and top views, respectively, of a second embodiment of the present invention implemented as an across grain linescanning device for longitudinal material feeding applications.
Figure 10:
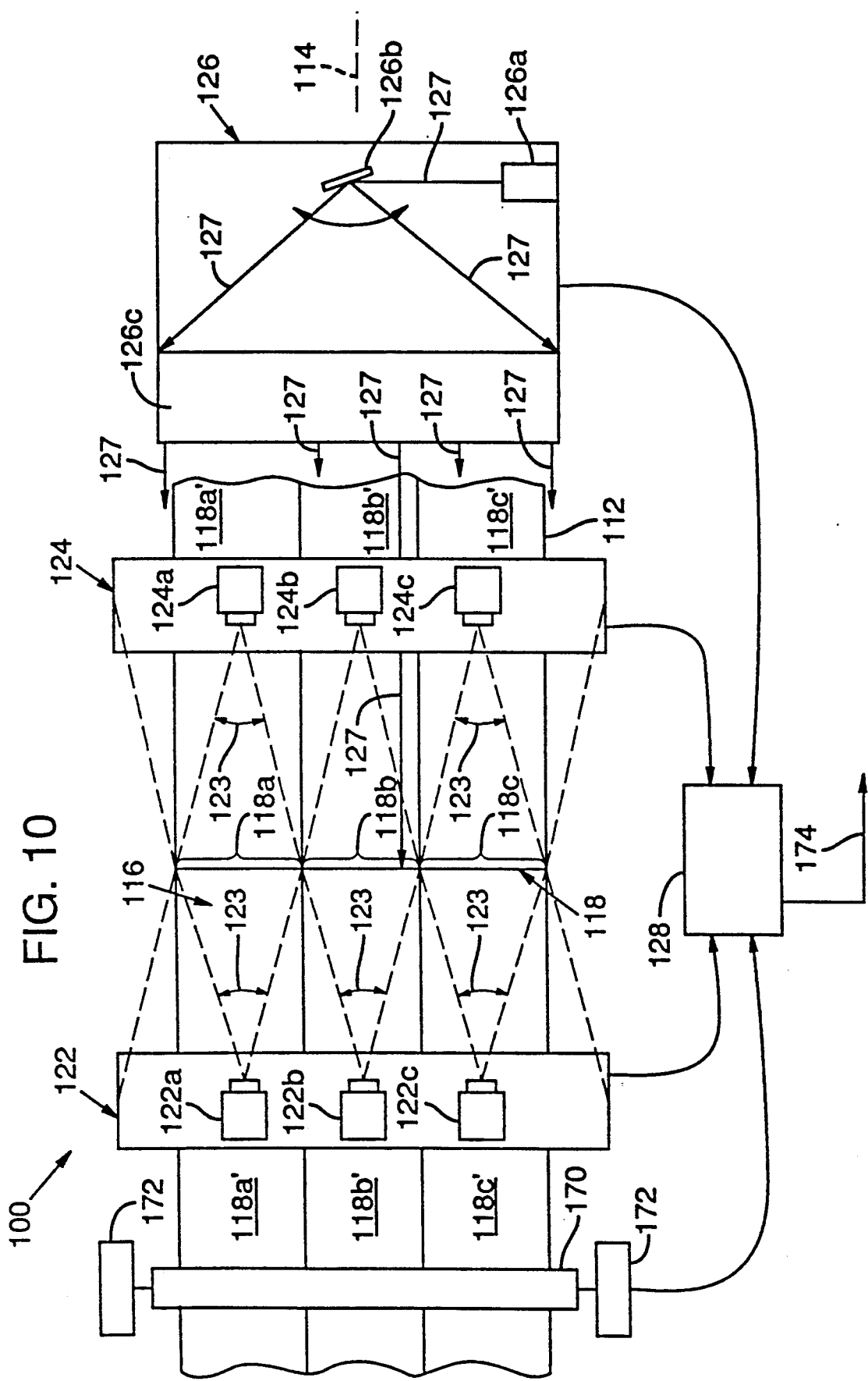

FIGS. 9 and 10 illustrate side and top views, respectively, of a second more practical embodiment of the present invention implemented as an across grain linescanning device for longitudinal material feeding applications. In FIGS. 9 and 10, an across grain linescanning apparatus 100 includes detector arrays 122 and 124, each including corresponding individual detectors 122a–122c and 124a–124c, respectively. In the illustrated embodiment, each of arrays 122 and 124 contains three detectors, but it should be apparent how the present invention may be practiced using arrays 122 and 124 with more or less than three detectors. As described more fully below, apparatus 100 defines an across grain inspection line 118 comprising contiguous transverse inspection sections 118a–118c. Apparatus 100 detects grain defects at surface 116 of a wood grain article 112 by movement of article 112 along its longitudinal axis 114 relative to apparatus 100 as by indexing rollers 170 and roller control 172. Roller control 172 provides to discrimination circuit 128 the article 112 position data whereby circuit 128 may associate a physical location on surface 116 for line 118 to with indexed position of article 112.

Corresponding detectors of arrays 122 and 124, e.g., detectors 122a and 124a, lie within separate and parallel planes of incidence (not shown) each orthogonal to the surface 116. In other words, each set of corresponding detector pairs is generally similar in arrangement and operational relation to that of detectors 22 and 24 (FIGS. 1 and 2). The output signals from corresponding detectors of arrays 122 and 124 are compared as described above for detectors 22 and 24 to detect grain defects where each set of corresponding detectors inspects a corresponding one of transverse inspection sections 118a–118c of surface 116. For example, the transverse inspection section 118a is subject to grain defect inspection by comparing the output of detectors 122a and 124a. Movement of article 112 along its longitudinal axis 114 while performing grain defect inspection at inspection sections 118a–118c accomplishes inspection along corresponding longitudinal areas 118a'–118c' whereby the surface 116 is inspected for grain defects.

Light source 126 of apparatus 100 includes a laser source 126a directed at a deflecting mirror 126b which in turn projects light beam 127 through a telecentric lens/mirror assembly 126c. This arrangement may be known to those skilled in the art as a telecentric flying spot linescanning system whereby light beam 127 remains substantially parallel to a plane orthogonal to surface 116 and containing axis 114 and maintains a given angle of incidence 154. This longitudinal orientation for light beam 127 is important as it maintains a longitudinal orientation for the cone 44 (FIG. 6) according to the specular diffuse light reflection model. With light beam 127 tracing across the grain of article 112 as described, diffuse reflection measured by corresponding detectors is similar due to the symmetry of such diffuse reflection and symmetric selected positioning of corresponding detectors within arrays 122 and 124. Accordingly, each detector of a pair of corresponding detectors, e.g., detectors 122b and 124b, measures similar light intensity for diffuse reflection from surface 116.

Specular diffuse reflection, however, is not symmetric. This asymmetry relates the detector maximum spacing to detector view angle, i.e. relates the maximum spacing between detectors within each array 122 and 124 is taken as a function of detector view angle. According to the specular diffuse reflection model, as the light beam 127 moves transversely across the article 112 at a given angle of incidence, the cone 44 (FIG. 6) similarly moves transversely across article 112. The detectors within array 122 must be spaced so as to maintain a view angle including the surface of cone 44 such that the specular component 42 of reflected light, when present, may be detected. More particularly, the view angle of each detector of array 122 includes the arc 45 (FIG. 6) so long as the light beam 127 is incident at the corresponding transverse portion of line 118. In a practical application, view angles on the order of +/- twelve degrees should be adequate. Thus, by maintaining proper spacing between detectors 122, i.e., not too far apart, specular reflection from beam 127 as it moves through each of transverse sections 118a–118c is appropriately detected by a corresponding one of detectors 122a–122c, respectively.

Another aspect of the selected placement of the detector arrays 122 and 124 requires, in a flying spot implementation, that the detector array 122, i.e., the specular detector array, be positioned somewhat off of the precise line of specular reflection in order to avoid large magnitude variations in detector output. More particularly, as the light beam 127 traces laterally across the surface 116, each of the detectors in detector array 122 will be exposed to the reflected light intensity for a period of time as the light beam 127 passes across the detector field of view. If the detector arrays are positioned so as to view the inspection section directly along the line of specular reflection, then large magnitude variation in detector output occurs as the detector suddenly becomes exposed to the maximum intensity of available specular reflection.

To avoid such large magnitude detector output variations, it is suggested that the detector array 122 be positioned slightly off the exact line of specular reflection. With reference to FIG. 9, the angle 146, as measured relative to a vertical reference line perpendicular to the surface 116, represents the line of sight for the detector array 122. The angle 154 represents both the line of sight for the detector array 124 and, approximately, the angle of incidence for the light beam 127. The angle 146 should be varied on the order of at least 5 to 15 degrees relative to the angle 154. By such placement of the detector array 122, the detector array 122 is positioned to detect predominately specular reflection, yet is not suddenly exposed to the full intensity of the specular reflection and thereby enjoys a more uniform detector output.

As may be appreciated, the detector array 124 has greater freedom of positioning and need not necessarily be positioned as viewing the inspection line substantially along the line of incidence. Because the diffuse reflection measured by the detector array 124 is more uniform, it is possible to place the detector array in a variety of positions so long as the detector array 124 is not exposed to predominately specular reflection.

In operation, article 12 is moved along its longitudinal axis 114 relative to apparatus 100 as light beam 127 traces across its grain to define the line 118. Light source 126 provides to discrimination circuit 128 the light beam 127 position data, i.e., its transverse position along line 118. As previously noted, index roller control 172 provides the article 112 position data to discrimination circuit 128. The light beam 127 position data from light source 126 together with the article 112 position data from roller control 172 provides to discrimination circuit 128 sufficient information to associate a physical location on surface 116 corresponding to a current point of incidence for light beam 127. By suitably sampling data from arrays 122 and 124 in coordination with knowledge of the actual point of incidence of light beam 127, discrimination circuit 128 constructs data 174 as output representing surface 116. For example, as light beam 127 moves through inspection section 118b, discrimination circuit 128 collects data from detectors 122b and 124b at given rate corresponding to a given number of points along section 118b, and calculates a corresponding set of ratio values thereof, so as to identify grain defects along the corresponding portion of surface 116. Surface 116 representation data 174 is then made available to subsequent wood processing steps to maximize use of article 112.

The present invention has shown an inherent ability to discriminate not only between normal grain patterns and grain defects, but also between wood and certain grading marks thereon, particularly felt tip ink marks and wax crayon marks. Ink is taken up more readily by the diffuse related wood structures, i.e., cell cavities, resin, etc., than by the specular diffuse related components, i.e., the cellulose fibers in the cell walls. This suppresses the diffuse detector 24 output much more than the specular diffuse detector 22 output such that the ratio of detector 22 to detector 24 output rises to a very high level, higher than that associated with clearwood. This high ratio in connection with an unusually low detector 24 output yields a clear "ink signature." In knotwoods the specular diffuse components are virtually nonexistent and the ratio for knotwoods remains unchanged when marked by ink. Accordingly, ink marks upon knotwood may not be detectable. As for wax crayon marks, the wax provides a specular surface on the wood while the wax pigment suppresses the diffuse reflection. Again this yields a very high detector output ratio, but with a characteristic low specular diffuse detector 22 output. Wax marks are generally detectable whether on knotwood or clearwood.

Figure 11:
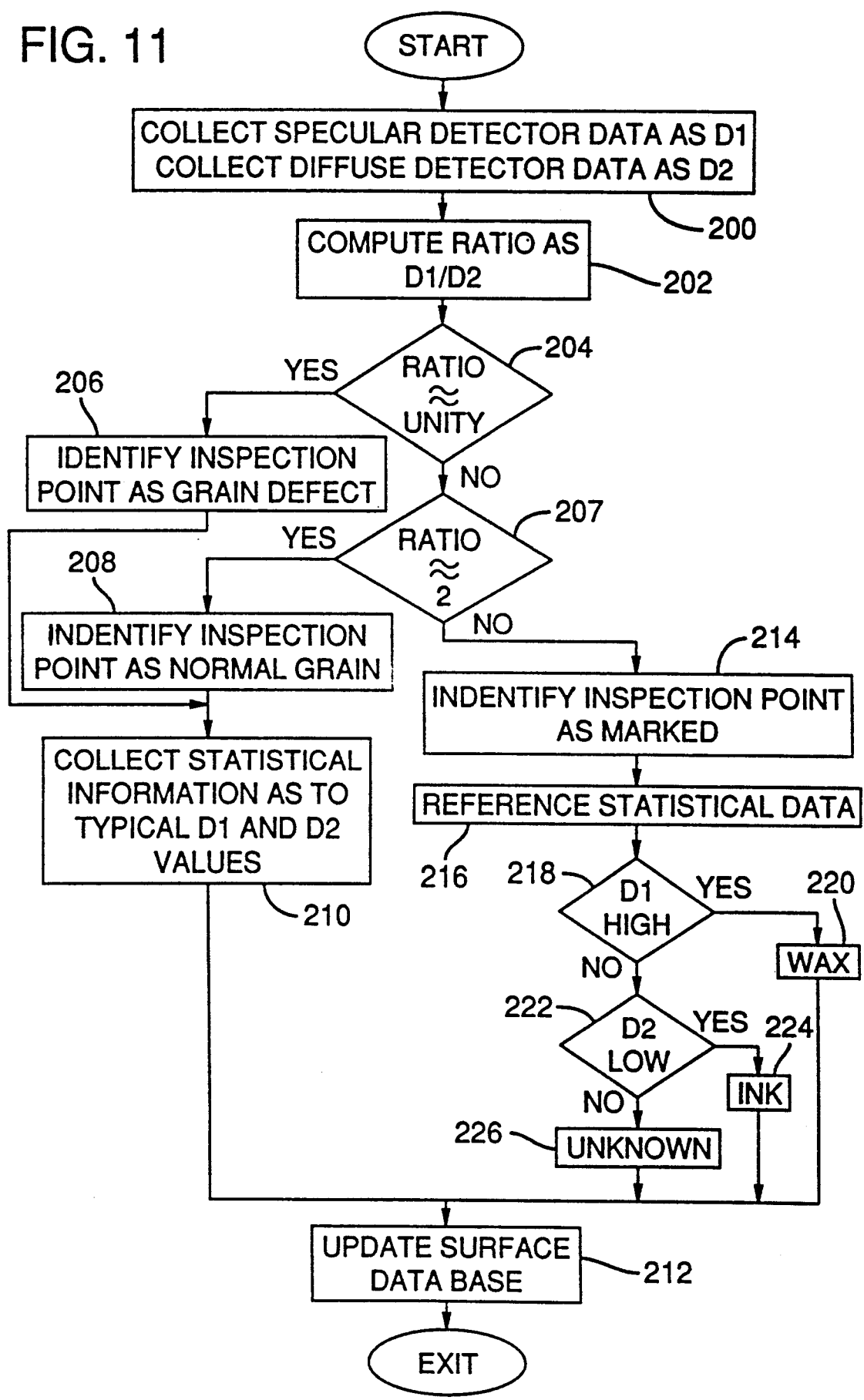
FIG. 11 is a flow chart illustrating steps associated with operation of the device of FIGS. 1 and 2.

FIG. 11 is a flow chart illustrating operation of the device of FIGS. 1 and 2 for each indexed inspection point including discrimination of grain defects as well as ink and wax markings on wood article 12. It should be apparent to those skilled in the art how the steps illustrated in FIG. 11 may be applied to the device of FIGS. 9 and 10. More particularly, the steps illustrated in FIG. 11 correspond to each sampling of data taken from corresponding detector points of arrays 122 and 124.

In FIG. 11, processing by discrimination circuit 28 of each sampling of data collected from detectors 22 and 24 begins in block 200 where the output of the specular detector 22 is stored in the variable D1 and diffuse detector 24 output is stored in the variable D2. In block 202 discrimination circuit 28 computes the ratio D1/D2 for storage in the variable RATIO. The value of RATIO will determine branching through the flow chart and actual RATIO values for branching decisions will vary depending on the application. In decision block 204 the value of RATIO is compared to unity. If substantially equal to unity, e.g. below the value 1.3, processing branches to block 206 where discrimination circuit 28 identifies the portion of surface 16 corresponding to inspection point 18 as a grain defect. A negative result in block 204 passes processing control to decision block 207. If decision block 207 determines that the value of RATIO is approximately equal to the value two, e.g. in the range of 1.3 to 2.4, processing branches to block 208 where discrimination circuit 28 identifies the portion of surface 116 corresponding to inspection point 18 as a normal grain pattern. Processing from either of blocks 206 or 208 continues to block 210 where discrimination circuit 28 stores the values D1 and D2 and maintains statistical data representing typical D1 and D2 values useful in discriminating between ink and wax marks. Continuing to block 212, discrimination circuit 28 incorporates the identification of the inspection point 18, e.g. grain defect or normal grain pattern, by updating a surface 16 database structure.

If decision block 207 determines that RATIO is not substantially equal to the value two, e.g. greater than the value three, processing branches to block 214 where the portion of surface 16 corresponding to inspection point 18 is identified as being marked either by ink or wax. Should discrimination between ink and wax markings be desired, block 216 references statistical data previously stored as typical D1 and D2 values. Decision block 218 tests for an unusually high D1 value, inferring a wax mark in block 220, and decision block 222 tests for an unusually low D2 value, inferring in block 224 an ink mark. If decision block 222 determines that D2 is not unusually low, the type of marking is identified as unknown in block 226. In any case, processing eventually reaches block 212 where discrimination circuit 28 would suitably update the surface 16 database structure relative to the corresponding portion of surface 16 as being marked, either by wax, by ink, or unknown. After scanning the entire surface 16, the surface 16 data structure may be referenced to identify the location of grain defects as well as interpret detected ink and wax markings thereon.

Figure 12:
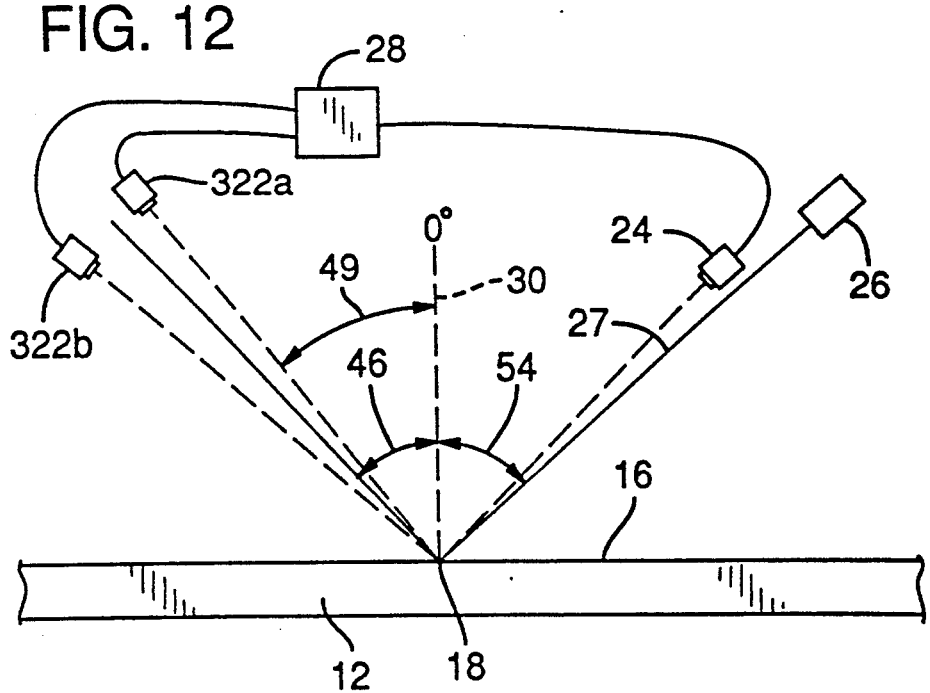
FIG. 12 illustrates a modification for more accurate detection of knotwood dimensions applicable to the embodiments of the present invention illustrated herein.

FIG. 12 illustrates a modification applicable to both of the illustrated embodiments of the present invention for more accurately determining the dimension of knotwood. The modification will be described with reference to the embodiment of FIGS. 1 and 2. There exists an extensive region below knots, toward the butt of the log from which the sample has been cut, where the grain carries a diving component, i.e. the direction of the wood fiber has a component oriented into the surface 16. The ratio of detector 22 output to detector 24 output, being greater than unity, for this region will correctly indicate clearwood, but the actual specular reflection peak angle deviates from the specular angle defined by the surface 16 of article 12. This reduces the ratio of detector 22 output to detector 24 output and this can extend the apparent dimension of knots. FIG. 8 illustrates this deviation. In FIG. 8, detector 22 output for clearwood response 50 does not actually peak at the specular angle 46, rather at an adjacent angle 49. Angle 49 may be on either side of angle 46 depending on the direction of material feeding, i.e. whether the butt end leads. It may be desirable to detect the peak value for the specular component of reflected light so as to maximize the calculated detector 22 to detector 24 output ratio. Should it be desirable to minimize the effect due to such diving grain, it is suggested that a pair of detectors, 322a and 322b in FIG. 12, replace detector 22. Detectors 322a and 322b are positioned above and below, respectively, the specular reflection angle 46 and their outputs are appropriately combined to capture the peak specular value and produce what would otherwise be detector 22 output.

In typical applications of the illustrated embodiment, the angle of incidence 54 is on the order of 45 degrees and the diameter of light beam 27 is on the order of one to two millimeters. Light polarization orientation may be optimized in some applications, but has generally been found satisfactory at a variety of polarization orientations.

In certain hardwood species, the "ring porous" types, there are wide bands of large cells ("vessels") that appear on the face of a surfaced board. These vessels can be on the order of 1 mm by 4 mm in size, and form relatively large pits when the wood is surfaced. Typical species are the red and white oaks, where these bands of vessels give the wood surface an appearance that is usually desirable for its use in furniture or trim moldings. Unfortunately, these cells can also strongly scatter and absorb light beam 27 since the cell size is large enough to encompass the typical collimated laser beam used in this application. Further, in certain species a structure called "tyloses" forms in the vessels and absorbs the optical radiation even more strongly.

To address this problem with ring porous type hardwoods, the apparatus 20 may be adapted in three ways. The adaptation will be described with reference to the embodiment of FIGS. 1 and 2, but is equally applicable to the embodiment of FIGS. 9 and 10. First, increase the angle of incidence 54 to about fifty-five degrees. Second, increase the laser spot size, i.e. the area of point 18, in the cross scan direction, i.e. along the normal grain direction to 4 or 5 mm to provide an elongate area of incidence. This is achieved with a cylindric lens in the laser path, usually pre-scan This will not increase the spot size in the orthogonal direction (across the grain). Such elongation in the scan direction would decrease the ability of the apparatus 20 to resolve the edge of the defect areas. Third, orient the laser polarization parallel to the plane of incidence 25. These adaptations are not required for other hardwoods (the "diffuse-porous" species), or for softwood species, which do not have vessels. The increases in angle of incidence 54 and area of point 18 are not generally desirable, but represent a trade-off in order to better detect defects in the ring porous species It should be apparent to those skilled in the art how these adaptations may be applied to the apparatus 100 of FIGS. 9 and 10.

Thus, a method and apparatus for detection of grain defects by reflective scanning has been shown and described. The method and apparatus according to the present invention is an inherently simple and low cost technology. The method and apparatus has provided excellent discrimination for knotwood, both live and dead, in a wide range of solid wood products such as softwood veneers, hardwood and softwood boards, and shingles. The method and apparatus is useful in a wide range of surface conditions such as characterization of dirty, stained, rough cut, knife planed, or abrasive planed surfaces.

While the present invention has been illustrated in the context of longitudinal material feed applications, it should be apparent that the invention may be practiced in transverse material feed applications. Under such transverse material feed applications the orientation of the light beam directed toward the wood grain surface remains with reference to the fiber structures, i.e., grain pattern, of the surface. For example, and with reference to FIG. 6, the article 12 may be transported past the inspection point 18 by movement in a direction perpendicular to the longitudinal axis 14 of the article 12. In such movement, the light beam 27 maintains the same orientation with respect to the wood grain structures of the surface 16, but would provide information for a lateral inspection line, as opposed to the longitudinal inspection line 18'. While the above example illustrates the basic operation of a transverse material feed application of the present invention, such an arrangement is not very useful as it would deliver rather sparse data along the length of the wood product.

Figure 13:
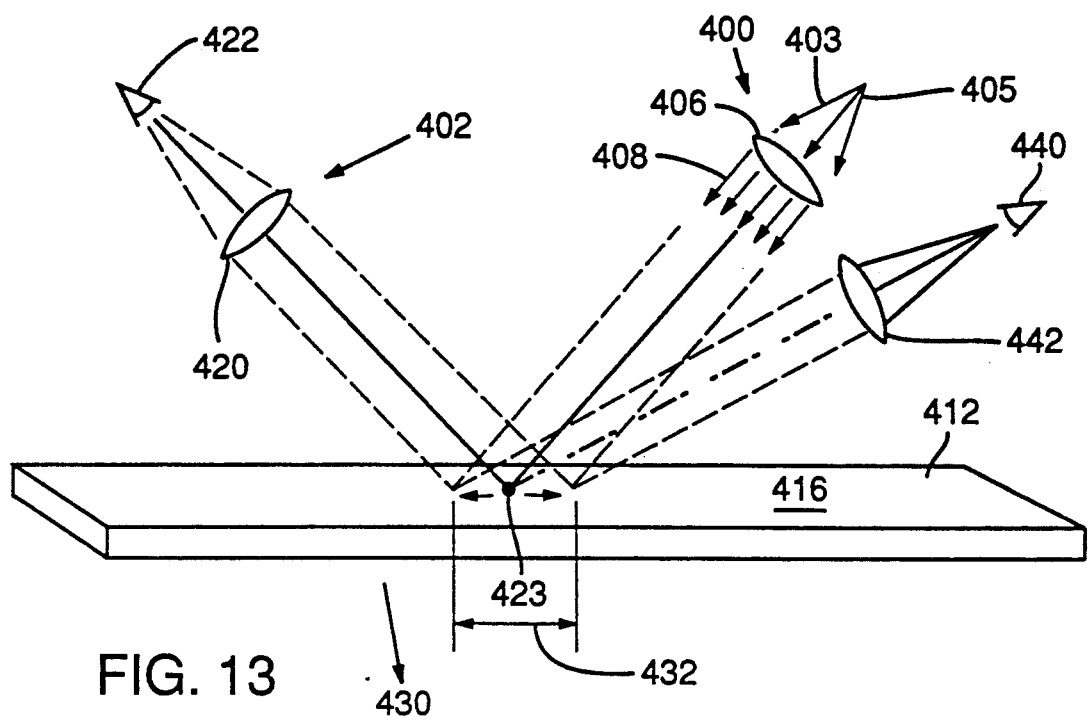
FIG. 13 illustrates use of a telecentric light source and telecentric light detector arrangement for use in transverse material feed application.

FIG. 13 illustrates a more practical transverse material feed application using a telecentric light source 400 and a telecentric light detector 402 in implementation of the present invention. The source 400 includes a scanned laser beam 403 operating in a plane normal to the surface 416 and lying along the normal grain direction of the wood product 412. The center of the scanning beam 403 lies at the focal point 405 of lens 406. Thus, the outgoing beam 408 is scanned at a constant angle relative to surface 416, and moves along the length portion 432 at a constant angle of incidence. Telecentric light detector 402 is positioned with reference to the orientation of surface 416 and the constant angle of incidence of collimated light 408, i.e., generally along the angle of reflection for the light beam 408 relative to the surface 416. Detector 402 includes a lens 420 and a detector 422 at the focal point of lens 422 so as to collect the portion of light 408 reflected from surface 416 and traveling generally along the specular angle of reflectance. As may be appreciated, components of light 408 not traveling generally along the specular angle of reflectance will not hit the detector 422. Thus, as the light beam 403 is scanned a moving inspection point 423 moves along the length portion 432 of wood product 412 and the detector 422 receives reflected light from the inspection point 423. A diffuse detector 440 also views the inspection point 423 through a lens 442, but at an angle relative to surface 416 greatly separated from the angle of reflectance. By comparing the output magnitudes of the detectors 422 and 442 the grain structure at inspection point 423 may be characterized as described herein above. By moving the wood product 412 transversely, i.e., in a direction 430, the entire width of wood product 412 along the length portion 423 is suitably scanned. As may be appreciated, additional telecentric light sources and detectors may be employed to scan other portions of the wood product 412, i.e., the width of wood product 412 at length portions other than that of length portion 432. In this manner, the entire surface 416 may be scanned according to the present invention.

As may be appreciated, other light source and detector arrangements can be employed in implementation of the present invention. For example, wherein the above example the inspection point 423 was defined by the scanning laser beam 403, it is possible to define the inspection point 423 by means of a scanned detector. More particularly, the source could be a steady source like a tungsten halide bulb providing a bright and substantially single point light source directed through a lens in order to provide a light plane substantially normal to the surface 416, lying along the grain structure of the product 412, and at a given angle of incidence. The specular and diffuse scanning detectors could then be provided such as by a linear array photodiode detector. Then instead of the point of inspection being defined by the laser beam position, the point of inspection is defined by the individual active photo detector position along the array.

Thus, by suitably orienting the light beam relative to the wood grain structures, and suitably selecting and positioning the detectors with reference to the orientation and character of the light beam, it is possible to characterize the structure of the wood grain article regardless of the direction of travel, i.e., longitudinal feeding verses transverse feeding, of the article 12. Furthermore, it may be appreciated that the present invention may be applied to inspect a stationary article with appropriate illumination and light detection apparatus.

While the present invention has been illustrated by use of a collimated relatively narrow width light source and detectors having relatively larger view angles, it may be appreciated that the present invention may be implemented in other illumination and detection arrangements. For example, a collimated flood light may be directed at a given angle of incidence to a board surface or surface area in order to produce both diffuse and specular-diffuse reflection for detection by, for example, line or area array detectors. In this arrangement, the board could be stationary or could be moving relative to the light detectors. Similarly, the light source could be provided by a lens producing a light plane illuminating a line segment of the board surface. In such arrangement, it would be desirable to provide detectors with sufficiently narrow view angles so as to define a relatively small area of board surface under inspection.

Thus, while the illustrated embodiments define the area of inspection by use of a narrow light beam, a wider or larger area of the board may be illuminated and more precise detection apparatus may be employed to define a small inspection area. Accordingly, a great variety of light source and light detection arrangements may be used in implementation of this invention. Such arrangements would include the use of linear and area array detectors; collimated light beams, light planes, or wide area light columns; narrow and wide view detectors; and variation in the direction of travel, or no travel, of the article relative to the detection system. In any system, it is contemplated that the orientation of the energy source toward the wood grain article be with reference to the orientation of the structures, i.e., orientation of fiber structures, of the wood grain article such that the appropriate energy reflection patterns are generated in order to detect and differentiate between predominately specular reflection and predominately diffuse reflection in order to characterize the article under inspection.

Figure 14:
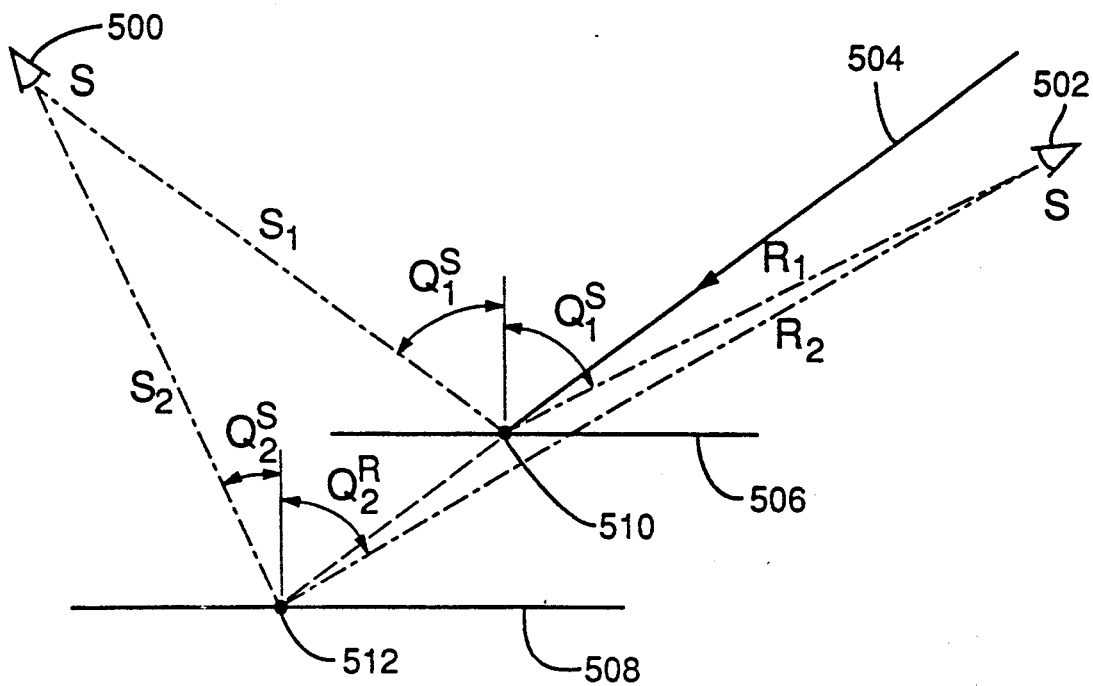
FIG. 14 illustrates an enhancement for adapting to variation in wood product height in practice of the present invention.

While not essential to practice of the broader aspects of the present invention, it is contemplated that adaptation in signal processing may be employed where height variation in the inspected wood products occurs. FIG. 14 illustrates the effect of height variation relative to data collected by the detectors of the present invention. In this example the S detector 500 represents the specular detector and the R detector 502 represent the diffuse detector. Two possible heights, upper height 506 and lower height 508, for the inspection surface of a wood product are shown along with the various angular relationships between the light beam 504 and lines of sight for each of detectors 500 and 502. The light beam 504 coincides with the height 506 at the inspection point 510 and the with the height 508 at the inspection point 512.

The distances $S_1$ and $S_2$ correspond to the distances between the S detector 500 and the inspection points 510 and 512, respectively. Similarly, the distances $R_1$ and $R_2$ correspond to the distances between the R detector 502 and inspection points 510 and 512, respectively. The angles $\theta^R_1$ and $\theta^R_2$ correspond to the angle, expressed relative to a vertical reference, of the line of sight for R detector 502 at the inspection points 510 and 512, respectively. The angles $\theta^S_1$ and $\theta^S_2$ correspond to the angle, expressed relative to a vertical reference, of the line of sight for R detector 502 at the inspection points 510 and 512, respectively.

For a given range of variation in the heights 506 and 508, the distances $S_1$ and $S_2$ will be approximately equal and the angles $\theta^S_1$ and $\theta^S_2$ will differ slightly. Conversely, the distances $R_1$ and $R_2$ will more widely vary relative to one another and the angles $\theta^R_1$ and $\theta^R_2$ will not differ significantly relative to one another. Because the intensity of light energy at the detectors falls as the inverse of square of distance to the inspection point, variation in heights 506 and 508 affects the output of R detector 502 much more than that of S detector 500. For example, a system calibrated for height 506, with distances $R_1$ and $S_2$ being substantially equal, will establish a given threshold, i.e. a given detector output ratio, to detect grain defects. For height 508, however, this threshold may not be appropriate because at height 508 the R detector 502 output is more greatly attenuated relative to the output of S detector 500, i.e. $R_2$ is not substantially equal to $S_2$.

Thus, it is contemplated that the use of detector output magnitudes, i.e. ratio calculation, take into account height variation relative to a given reference or calibration height. This may be done in a variety of ways. For example, by first detecting or measuring inspection surface height relative to a reference or calibration height it is possible to algorithmicly correct, i.e. boost or attenuate, the S detector 502 output, either in hardware or software, in order to maintain a "unity" threshold. Alternatively, the threshold itself could vary as a function of the detected variation in height relative to the reference or calibration height. As may be appreciated, many other methods may be employed to adapt to variation in inspection surface height.

While a preferred embodiment of the present invention has been shown and described, it will be apparent to those skilled in the art that modifications relative to the illustrated embodiment are possible without departure from the scope of the invention. For example, it is believed that the present invention may be practiced by a variety of techniques beyond light energy scanning such as acoustics or any other form of energy that undergoes specular-diffuse reflection as understood and presented herein. It will be appreciated, therefore, that the scope of the present invention is not restricted to the particular embodiment that has been described and illustrated, but rather includes any modifications as fall within the appended claims and equivalents thereof.

We claim:

1. A method of characterizing an energy reflective wood grain surface structure defining a longitudinal axis thereof, said method comprising:
    directing an energy source along a line of incidence to an inspection point of said wood grain surface structure, said line of incidence being substantially co-planar with said longitudinal axis of said wood grain surface structure;
    monitoring first reflective energy emanating from said inspection point along a line of reflection corresponding to a specular angle of reflection relative to said line of incidence and said inspection point;
    monitoring diffuse second reflective energy emanating from said inspection point along a line other than said line of reflection; and
    calculating a ratio of said first and second reflective energy to characterize said wood grain surface structure at said inspection point.

2. The method according to claim 1 wherein said ratio characterizes said inspection point as one of predominately specular reflective or predominately diffuse reflective.

3. The method according to claim 1 wherein said energy source is a light energy source.

4. A method of characterizing a wood grain surface structure, the method comprising:
    directing a light beam upon said wood grain surface structure at a given angle of incidence;
    detecting diffuse reflected light from said wood grain surface structure and resulting from said light beam;
    detecting predominately specular reflected light from said surface as defined by said given angle of incidence and resulting from said light beam;
    computing a ratio of said specular reflected light to said diffuse reflected light; and
    characterizing said surface in response to said computed ratio.

5. The method according to claim 4 wherein said wood grain surface structure is the surface of a wood grain article and said characterizing step includes characterizing said surface at a point of incidence of said light beam as being normal wood grain structure in response to said computed ratio being substantially greater than unity and as being a grain defect in response to said ratio being substantially equal to unity.

6. A method of characterizing surface grain structure features of an elongate wood grain article, said grain structure lying generally along the longitudinal axis of said article, the method comprising:
    directing a collimated light beam at the surface of said wood grain article and along an angle of incidence relative to said surface, said light beam being within an incidence plane substantially orthogonal to said surface, said light beam being incident upon said surface at an incidence point at said surface, said incidence plane being substantially parallel to said longitudinal axis;
    detecting first and second reflected light energy of said light beam from said incidence point at first and second detection locations, respectively, within said incidence plane, the first location being generally along a surface specular angle as defined by said angle of incidence; and
    characterizing surface features at said incidence point by computing a ratio of said first and second reflected light energy.

7. A method according to claim 6 wherein said incidence point is characterized as a grain structure defect in response to said ratio being computed as near unity and characterized as clearwood in response to said ratio being computed as being substantially greater than unity.

8. A method according to claim 6 wherein said step of characterizing surface grain structure features comprises identifying at said incidence point the presence of at least one of a normal grain structure, a grain defect, an ink mark, and a wax crayon mark.

9. A method of distinguishing a grain structure defect and a normal grain structure at an inspection point at the surface of a wood grain article, the method comprising:
    directing a light beam at said inspection point whereby light is reflected from said inspection point, said light beam having an angle of incidence relative to said surface;
    measuring at a first detection point a first reflected light intensity from said inspection point substantially along a specular angle of reflection relative to said angle of incidence;
    measuring at a second detection point a second reflected light intensity from said inspection point at an angle of reflection other than said specular angle of reflection;
    computing a ratio of said first reflected light intensity to said second reflected light intensity; and
    identifying said inspection point as corresponding to normal grain structure when said ratio is substantially greater than unity and identifying said inspection point as corresponding to a grain structure defect when said ratio is substantially equal to unity.

10. A method according to claim 9 wherein said inspection point, said first detection point, and said second inspection point are co-planar within an incidence plane orthogonal to said surface and aligned with the normal grain direction of said article.

11. A method according to claim 10 wherein said first and second detection points are substantially equidistant from said inspection point and substantially symmetric with respect to an axis normal to said surface and within said incidence plane.

12. A method according to claim 9 wherein said first and second detection points are substantially equidistant from said inspection point.

13. A method according to claim 9 wherein said article is a ring porous type hardwood species, said angle of incidence is substantially 55 degrees relative to a vector normal to said surface and coincident with said inspection point, and said inspection point is an elongate area of said light beam as incident upon said surface.

14. A method according to claim 9 wherein said measurement of first reflected light energy is taken along a first line of sight from said inspection point, said first line of sight being at a given angular offset relative to said specular angle of reflection as defined by said angle of incidence relative to said surface and by said inspection point, and wherein said measurement of second reflected light energy is taken along a second line of sight from said inspection point, said second line of sight being more greatly angularly offset from said specular angle of reflection than that offset of said first line of sight.

15. The method according to claim 14 wherein the angular offset of said first line of sight relative to said specular angle is between zero and twenty degrees.

16. A device for identifying grain defects in a wood grain surface structure having a longitudinal axis and at an inspection point at the surface of a wood grain article, the device comprising:
a light source directing a beam of light to said inspection point, said beam of light being within an incidence plane orthogonal to said surface, generally co-planar with said longitudinal axis of said wood grain structure, and having an angle of incidence relative to said surface;
a first light detector positioned at a given distance from said inspection point within said incidence plane and adapted to provide a first output signal representative of reflected light intensity emanating from said inspection point and substantially along a specular angle of reflection with respect to said angle of incidence;
a second light detector positioned at said given distance from said inspection point within said incidence plane and adapted to provide a second output signal representative of reflected light intensity emanating from said inspection point and substantially along said angle of incidence; and
discrimination means for identifying grain defects at said inspection point, said discrimination means including means for receiving said first and second output signals and for computing a ratio of said first output signal magnitude to said second output signal magnitude whereby in response to a computed ratio substantially equal to unity said discrimination means identifies a grain defect at said inspection point and in response to a computed ratio substantially greater than unity said discrimination means identifies clearwood at said inspection point.

17. A device according to claim 16 wherein said light beam is a collimated light beam.

18. A device according to claim 16 wherein the lines of sight from each of said first and second light detectors to said inspection point are substantially symmetric about an axis normal to said surface and coincident with said inspection point.

19. A method of characterizing an energy reflective wood grain surface structure defining a longitudinal axis thereof, said method comprising:
directing an energy source along a line of incidence to an inspection point of said wood grain surface structure, said line of incidence being substantially co-planar with said longitudinal axis of said wood grain surface structure;
monitoring first reflective energy emanating from said inspection point along a line of reflection positioned with reference to a specular angle of energy reflection as defined by said line of incidence and by said inspection point;
monitoring diffuse second reflective energy emanating from said inspection point along a second line of reflection more greatly angularly offset from said specular angle than that of said first line of reflection; and
calculating a ratio of said first and second reflective energy to characterize said wood grain surface structure at said inspection point.

20. The method according to claim 19 wherein said ratio characterizes said inspection point as one of predominately specular reflective or predominately diffuse reflective light energy.

21. The method according to claim 19 wherein said energy source is a light energy source.

22. The method according to claim 19 wherein said first line of reflection is sufficiently close to said specular angle whereby said first reflective energy is predominately specular energy reflection when present and said second line of reflection is sufficiently angularly offset from said specular angle to respond to predominately diffuse energy reflection.

23. The method of claim 19 wherein said energy source is a telecentric flying spot light source and said first line of reflection is angularly offset from said specular angle by at least 5 degrees and not more than 20 degrees.

24. The method according to claim 19 wherein said energy source is a collimated light beam of given dimension and said first and second reflective energies are taken through view angles substantially greater than said given dimension whereby said light beam defines the area of said inspection point.

* * * * *